(12) United States Patent
Weber et al.

(10) Patent No.: US 8,026,943 B2
(45) Date of Patent: Sep. 27, 2011

(54) SURFACE MAPPING AND GENERATING DEVICES AND METHODS FOR SURFACE MAPPING AND SURFACE GENERATION

(75) Inventors: Gerhard Weber, Inning (DE); Albert Mehl, Holzkirchen (DE); Stephan Holzner, Mühldorf am Inn (DE); Wolfram Gloger, Weilheim (DE)

(73) Assignee: Institut Straumann AG, Basel (CH)

( * ) Notice: Subject to any disclaimer, the term of this patent is extended or adjusted under 35 U.S.C. 154(b) by 340 days.

(21) Appl. No.: 12/026,617

(22) Filed: Feb. 6, 2008

(65) Prior Publication Data

US 2008/0131833 A1 Jun. 5, 2008

Related U.S. Application Data

(63) Continuation of application No. 10/427,731, filed on May 1, 2003, now Pat. No. 7,399,181, which is a continuation of application No. PCT/DE01/04177, filed on Nov. 8, 2001.

(30) Foreign Application Priority Data

Nov. 8, 2000 (DE) .............................. 200 19 033 U
Jan. 24, 2001 (DE) .............................. 201 01 227 U

(51) Int. Cl.
H04N 7/18 (2006.01)
(52) U.S. Cl. .............................. 348/77; 348/135; 348/94
(58) Field of Classification Search ........... 375/240.01–240.29; 348/66, 77–79, 348/91–95, 135–141
See application file for complete search history.

(56) References Cited

U.S. PATENT DOCUMENTS 3,861,044 A 1/1975 Swinson, Jr.
(Continued)

FOREIGN PATENT DOCUMENTS
CA 2285326 10/1998
(Continued)

OTHER PUBLICATIONS

International Search Report for PCT/DE2001/04177 filed Nov. 8, 2001.
(Continued)

*Primary Examiner* — Andy Rao
(74) *Attorney, Agent, or Firm* — Martin Fleit; Paul D. Bianco; Fleit Gibbons Gutman Bongini & Bianco PL

(57) ABSTRACT

A surface mapping and generating device which has devices for the process and/or cost optimization, in particular raw material recovery devices, an automatic control of the intensity of a used laser light, devices for carrying out a calibrating procedure by evaluating overlap errors at matching points, devices for archiving especially three-dimensional data of the jaw and/or for modeling the bite position of the upper and the lower jaws, devices for the optimized preparation of at least one dental stump for the production and placement of a dental prosthesis thereon and/or devices for taking into consideration the bite position of the upper and lower jaws. It can be provided that the devices for the process and/or cost optimization are designed to ensure that two half frames showing different positions or views are evaluated, whereby preferably a pulsed laser for exposure purposes is included and/or that an image recording device, in particular a CCD chip, is arranged so as to ensure that lines, taking into account the Scheimpflug angle, are located perpendicular to the direction of travel of a measuring table. Methods according to the present invention use such devices and function correspondingly. In addition, the invention also makes available a patient data archiving system which comprises a chip card and/or decentralized data storage systems especially for dental data.

20 Claims, 10 Drawing Sheets

U.S. PATENT DOCUMENTS

| | | | |
|---|---|---|---|
| 4,478,580 A | 10/1984 | Barrut |
| 4,575,805 A | 3/1986 | Moermann et al. |
| 4,742,464 A | 5/1988 | Duret |
| 4,935,635 A | 6/1990 | O'Harra |
| 4,964,770 A | 10/1990 | Steinbichler et al. |
| 5,092,022 A | 3/1992 | Duret |
| 5,128,870 A | 7/1992 | Erdman et al. |
| 5,184,306 A | 2/1993 | Erdman et al. |
| 5,237,998 A | 8/1993 | Duret et al. |
| 5,257,203 A | 10/1993 | Riley et al. |
| 5,338,198 A | 8/1994 | Wu |
| 5,347,454 A | 9/1994 | Mushabac |
| 5,401,170 A | 3/1995 | Nonomura |
| 5,527,182 A | 6/1996 | Willoughby |
| 5,533,895 A | 7/1996 | Andreiko et al. |
| 5,587,912 A | 12/1996 | Andersson et al. |
| 5,690,490 A | 11/1997 | Cannon et al. |
| 5,718,585 A | 2/1998 | Dehoff et al. |
| 5,816,810 A | 10/1998 | Antonson |
| 5,857,853 A | 1/1999 | van Nifterick et al. |
| 5,873,721 A | 2/1999 | Willoughby |
| 5,879,158 A | 3/1999 | Doyle et al. |
| 5,880,962 A | 3/1999 | Andersson et al. |
| 5,967,777 A | 10/1999 | Kleing et al. |
| 5,975,893 A | 11/1999 | Chishti et al. |
| 5,989,029 A | 11/1999 | Osorio et al. |
| 5,995,650 A | 11/1999 | Migdal et al. |
| 6,015,289 A | 1/2000 | Andreiko et al. |
| 6,044,170 A | 3/2000 | Migdal et al. |
| 6,049,743 A | 4/2000 | Baba |
| 6,062,861 A | 5/2000 | Andersson |
| 6,099,314 A | 8/2000 | Kopelman et al. |
| 6,205,243 B1 | 3/2001 | Migdal et al. |
| 6,224,373 B1 | 5/2001 | Lee et al. |
| 6,231,339 B1 | 5/2001 | Sharky |
| 6,287,121 B1 | 9/2001 | Guiot et al. |
| 6,295,513 B1 | 9/2001 | Thackston |
| 6,364,660 B1 | 4/2002 | Durbin et al. |
| 6,430,258 B1 | 8/2002 | Spaak |
| 6,463,344 B1 | 10/2002 | Pavloskaia et al. |
| 6,532,299 B1 | 3/2003 | Sachdeva et al. |
| 6,533,737 B1 | 3/2003 | Brosseau et al. |
| 6,575,751 B1 | 6/2003 | Lehmann et al. |
| 6,600,168 B1 | 7/2003 | Geng |
| 6,618,717 B1 | 9/2003 | Karadimitriou et al. |
| 6,640,150 B1 | 10/2003 | Persson et al. |
| 6,694,212 B1 | 2/2004 | Kennedy |
| 6,697,164 B1 | 2/2004 | Babayoff |
| 6,766,217 B1 | 7/2004 | Hamada |
| 6,788,986 B1 | 9/2004 | Traber et al. |
| 6,832,877 B2 | 12/2004 | Hamada |
| 6,848,909 B1 | 2/2005 | Persson |
| 6,851,949 B1 | 2/2005 | Sachdeva et al. |
| 6,970,760 B2 * | 11/2005 | Wolf et al. ............... 700/163 |
| 7,006,952 B1 | 2/2006 | Matsumoto et al. |
| 7,020,325 B2 | 3/2006 | Park |
| 7,027,642 B2 | 4/2006 | Rubbert et al. |
| 7,035,702 B2 | 4/2006 | Jelonek et al. |
| 7,058,213 B2 | 6/2006 | Rubbert et al. |
| 7,065,243 B2 | 6/2006 | Boland et al. |
| 7,068,825 B2 | 6/2006 | Rubbert et al. |
| 7,092,784 B1 * | 8/2006 | Simkins ................... 700/163 |
| 7,110,594 B2 | 9/2006 | Jones et al. |
| 7,123,767 B2 | 10/2006 | Jones et al. |
| 7,197,179 B2 | 3/2007 | Rubbert et al. |
| 7,305,110 B2 | 12/2007 | Rubbert et al. |
| 7,333,874 B2 | 2/2008 | Taub et al. |
| 7,342,668 B2 | 3/2008 | Quadling et al. |
| 7,373,286 B2 | 5/2008 | Nikolskiy et al. |
| 7,379,584 B2 | 5/2008 | Rubbert et al. |
| 7,399,181 B2 | 7/2008 | Weber et al. |
| 7,596,287 B2 | 9/2009 | Wolf et al. |
| 7,609,875 B2 | 10/2009 | Liu et al. |
| 7,689,310 B2 | 3/2010 | Kopelman et al. |
| 7,698,014 B2 | 4/2010 | Dunne et al. |
| 7,711,447 B2 | 5/2010 | Lu et al. |
| 7,724,932 B2 | 5/2010 | Ernst et al. |
| 7,899,221 B2 | 3/2011 | Weber |
| 7,905,725 B2 | 3/2011 | Chishti et al. |
| 2002/0027973 A1 | 3/2002 | Spaak |
| 2002/0028418 A1 | 3/2002 | Farag et al. |
| 2002/0036617 A1 | 3/2002 | Pryor |
| 2002/0044682 A1 | 4/2002 | Weil |
| 2002/0055800 A1 | 5/2002 | Nikolskiy et al. |
| 2002/0074675 A1 | 6/2002 | Meyertholen et al. |
| 2002/0081554 A1 | 6/2002 | Marshall |
| 2002/0137001 A1 | 9/2002 | Cipolla et al. |
| 2002/0137011 A1 | 9/2002 | Shoher et al. |
| 2003/0012423 A1 | 1/2003 | Boland et al. |
| 2003/0031977 A1 | 2/2003 | Bodenmiller et al. |
| 2003/0096214 A1 | 5/2003 | Luthardt |
| 2003/0123943 A1 | 7/2003 | Hamada |
| 2003/0131833 A1 | 7/2003 | Ponagai et al. |
| 2004/0032594 A1 | 2/2004 | Weber et al. |
| 2004/0078212 A1 | 4/2004 | Andersson et al. |
| 2004/0152036 A1 | 8/2004 | Abolfathi |
| 2004/0158342 A1 | 8/2004 | Wolf et al. |
| 2004/0197728 A1 | 10/2004 | Abolfathi |
| 2004/0220691 A1 | 11/2004 | Hofmeister et al. |
| 2004/0243481 A1 | 12/2004 | Bradbury et al. |
| 2005/0023710 A1 | 2/2005 | Brodkin et al. |
| 2005/0122518 A1 | 6/2005 | Overbeck et al. |
| 2005/0186540 A1 | 8/2005 | Taub et al. |
| 2005/0214716 A1 | 9/2005 | Weber et al. |
| 2006/0063135 A1 | 3/2006 | Mehl |
| 2006/0099549 A1 | 5/2006 | Engman |
| 2006/0106484 A1 | 5/2006 | Saligner et al. |
| 2007/0034347 A1 | 2/2007 | Bodenmiller |
| 2007/0128580 A1 | 6/2007 | Mormann |
| 2007/0154866 A1 | 7/2007 | Hall |
| 2008/0050700 A1 | 2/2008 | Weber et al. |
| 2008/0131833 A1 | 6/2008 | Weber et al. |
| 2008/0131841 A1 | 6/2008 | Taub et al. |
| 2008/0153067 A1 | 6/2008 | Berckmans et al. |
| 2008/0153069 A1 | 6/2008 | Holzner et al. |
| 2008/0154743 A1 | 6/2008 | Holzner et al. |
| 2008/0248443 A1 | 10/2008 | Chishti et al. |
| 2009/0081616 A1 | 3/2009 | Pfeiffer |
| 2009/0130633 A1 | 5/2009 | Kraemer et al. |

FOREIGN PATENT DOCUMENTS

| | | |
|---|---|---|
| DE | 4339746 A1 | 5/1995 |
| DE | 44 39 307 A1 | 5/1996 |
| DE | 4439307 | 5/1996 |
| DE | 4439307 A1 | 5/1996 |
| DE | A 44 39 307 | 5/1996 |
| DE | 196 05 741 | 7/1997 |
| DE | 19605741 | 7/1997 |
| DE | 19605741 C1 | 7/1997 |
| DE | 19642247 | 1/1998 |
| DE | 19710273 | 8/1998 |
| DE | 19710273 C1 | 8/1998 |
| DE | 197 21 688 | 9/1998 |
| DE | 19721688 | 9/1998 |
| DE | 19721688 A1 | 9/1998 |
| DE | A 197 21 688 | 9/1998 |
| DE | 19930564 | 10/2000 |
| DE | 20019033.4 | 11/2000 |
| DE | 20101227.8 | 1/2001 |
| DE | 20216119.6 | 10/2002 |
| DE | 102 14 968 | 10/2003 |
| DE | 202004009128 | 6/2004 |
| DE | 102006061134 A1 | 6/2006 |
| DE | 102006061143 | 12/2006 |
| DE | 102006061141 A1 | 7/2008 |
| EP | 0054785 A1 | 6/1982 |
| EP | 0054785 B1 | 7/1985 |
| EP | 0348061 A2 | 12/1989 |
| EP | 0490848 | 6/1992 |
| EP | 0643948 | 3/1995 |
| EP | 0 913 130 | 5/1999 |
| EP | 0913130 | 5/1999 |
| EP | 913130 | 5/1999 |
| EP | 0913130 A2 | 5/1999 |
| EP | 1 062 916 A2 | 12/2000 |
| EP | 1062916 | 12/2000 |
| EP | 1088620 | 4/2001 |

| | | |
|---|---|---|
| EP | 1208811 | 5/2002 |
| EP | 1293174 | 3/2003 |
| EP | 1 506 745 A1 | 2/2005 |
| EP | 1 558 893 | 8/2005 |
| EP | 1568335 A2 | 8/2005 |
| EP | 1782753 A2 | 5/2007 |
| ES | 2193450 | 5/1999 |
| JP | 05049651 | 2/1993 |
| JP | 200185060 | 7/2000 |
| JP | 2001054525 | 2/2001 |
| JP | 2001518815 | 10/2001 |
| WO | WO 94/27523 | 12/1994 |
| WO | WO 97/35439 | 9/1997 |
| WO | 98/44865 A1 | 10/1998 |
| WO | 99/13797 | 3/1999 |
| WO | 9926540 A1 | 6/1999 |
| WO | 9959106 A1 | 11/1999 |
| WO | 0019929 A1 | 4/2000 |
| WO | 01/32092 A1 | 5/2001 |
| WO | 01/76327 | 10/2001 |
| WO | WO 02/09612 | 2/2002 |
| WO | 02/39056 A1 | 5/2002 |
| WO | 0239056 A1 | 5/2002 |
| WO | WO 02/39056 | 5/2002 |
| WO | WO 02/076327 | 10/2002 |
| WO | 03/007834 | 1/2003 |
| WO | WO 03/007834 | 1/2003 |
| WO | WO 03/017864 | 3/2003 |
| WO | WO 03/024352 | 3/2003 |
| WO | WO 03/057067 | 7/2003 |
| WO | 03/105710 | 12/2003 |
| WO | 2004/004595 A2 | 1/2004 |
| WO | 2004/008981 A1 | 1/2004 |
| WO | WO 2004/030565 | 4/2004 |
| WO | 2004/038326 | 5/2004 |
| WO | WO 2004/037112 | 5/2004 |
| WO | WO 2004/038326 | 5/2004 |
| WO | WO 2004/044787 A | 5/2004 |
| WO | WO 2004/060197 | 7/2004 |
| WO | 2006/005284 | 1/2006 |
| WO | WO 2006/005284 | 1/2006 |
| WO | 2007117309 A2 | 10/2007 |

OTHER PUBLICATIONS

International Preliminary Examination Report PCT/DE2001/04177 filed Nov. 8, 2001.
European Search Report for EP 07001160.6 (European case related to U.S. Appl. No. 12/026,617).
European Search Report for EP 07001054.1 (European case related to U.S. Appl. No. 12/026,617).
European Search Report for EP 07001056.6 (European case related to U.S. Appl. No. 12/026,617).
International Preliminary Report on Patentability for PCT/DE2003/003462 filed Oct. 20, 2003.
International Search Report for PCT/DE2003/003462 filed Oct. 20, 2003.
European Search Report for 01 993 809.1 (European case related to U.S. Appl. No. 12/026,617).
Information Disclosure Statement for PCT/DE01/04177.
International Preliminary Examination report PCT/DE01/04177.
European Search Report issued Nov. 24, 2010 for EP07000790.
European Search Report issued May 14, 2007 for EP07001159.
European Search Report issued May 24, 2007 for EP07001161.
European Search Report issued May 22, 2007 for EP07001162.
European Search Report issued May 30, 2007 for EP0700912.
Fairpo, Jenifer E. H. et al.: Heinemann Dental Dictionary Fourth Edition; Reed Educational Professional Publishing Ltd. 1997.
Kucey, Brian K.S et al.: The Procera Abutment—The Fifth Generation Abutment for Dental Implants; Journal of the Canadian Dental Association 2000; 66: pp. 445-449; Sep. 2000, vol. 66, No. 8.
Lima Verde, Marcus A.R. et al.: Technique to Restore Unfavorably Inclined Implants; The Journal of Prosthetic Dentistry 1994;71: pp. 359-363 (Apr. 1994).
Felber, Leo et al.: Computergestutzte Vollautomatischekonstruktion Von Inlays; Acta Med Dent Helv, vol. 2:Sep. 1997, pp. 217-225.
Dental Dialogue: Das Internationale Journal fur die Zahntechnik; Mit freundlicher Empfehlung.
Notice of Opposition filed by 3M Innovative Properties Company for EP Appl. 03776796.9.
Annex I to Opposition filed by 3M Innovative Properties Company for EP Appl. 03776796.9.
Gerhard Geiger, Geschiepe Technik, 1982.
English translation of International Preliminary Examination Report published Apr. 18, 2005 for PCT/DE2003/003462 filed Oct. 20, 2003.
English translation of International Preliminary Examination Report published May 8, 2003 for PCT/DE2001/04177 filed Nov. 8, 2001.
English translation of International Preliminary Examination Report dated Dec. 28, 2006 for PCT/DE05/1037 published Jan. 19, 2006.
International Search Report dated Jun. 1, 2006 for PCT/DE05/1037 published Jan. 19, 2006.
English translation of Written Opinion dated Dec. 22, 2006 for PCT/DE05/1037 published Jan. 19, 2006.
For U.S. Appl. No. 11/954,339, filed Dec. 12, 2007 Final Rejection dated Jan. 25, 2011; and Office Action dated Jun. 4, 2010.
For U.S. Appl. No. 11/570,283, filed Oct. 22, 2007 Office Action dated Jul. 8, 2010 and Restriction Requirement dated Apr. 6, 2010.
For U.S. Appl. No. 11/095,027, filed Mar. 31, 2005 Response to Amendment under Rule 312 dated Jan. 20, 2011 and Notice of Allowance dated Sep. 28, 2010.
For U.S. Appl. No. 11/955,058, filed Dec. 12, 2007 Advisory Action dated Jan. 18, 2011; final rejection dated Nov. 3, 2010; Office Action dated Jun. 6, 2010, Restriction Requirement dated Mar. 29, 2010.
European Search Report for EP 08021006 mailed Mar. 8, 2011.
European Search Report for EP 10178863.6 mailed Mar. 10, 2011.
European Search Report for EP 10178872 mailed Mar. 11, 2011.
For U.S. Appl. No. 11/570,283 Final Office Action mailed Feb. 14, 2011.
For U.S. Appl. No. 11/095,027 Issue Notification dated Feb. 9, 2011.
For U.S. Appl. No. 11/955,058 Non-Final Office Action dated Mar. 2, 2011.

* cited by examiner

S1   B   S2   B   S3   B   S4   B   S5

State of the Art

State of the Art

State of the Art

State of the Art

SURFACE MAPPING AND GENERATING DEVICES AND METHODS FOR SURFACE MAPPING AND SURFACE GENERATION

CROSS REFERENCE TO RELATED APPLICATIONS

This application is a continuation of U.S. patent application Ser. No. 10/427,731, filed May 1, 2003, which in turn is a continuation of International Application No. PCT/DE01/04177 filed Nov. 8, 2001, the contents of which are here incorporated by reference in their entirety.

BACKGROUND OF THE INVENTION

1. Field of Invention

The present invention relates to a surface mapping and generating devices and to methods of surface mapping and surface generation. In particular and preferably, the present invention relates to devices and methods for mapping and/or generating surfaces of teeth.

2. Prior Art

The state of the art is exemplified by a prior-art device for the production of a dental prosthesis according to European Patent EP 98115809.0, and the technology disclosed in German Patents DE 44 39 307 A1 and DE 197 21 688 A1.

SUMMARY OF THE INVENTION

The basic technologies on which the present invention is based or with which it can be combined are disclosed in the German Patent Applications [Offenlegungsschrift] DE 44 39 307 A1 and DE 197 21 688 A1, which are used as the closest prior art, on the one hand, and which, by reference are hereby fully incorporated in the present documents, since the present invention in all of its embodiments is based on this technology, continues to develop and/or improves it advantageously, on the other hand, which is the objective of all of the aspects of the present invention.

This objective is implemented using devices and methods according to the claims. In particular, the invention makes available a surface mapping and generating device with devices for the process and/or cost optimization.

It is preferable for the process and/or cost optimization devices to comprise raw material recovery devices; also, it is preferable for the process and/or cost optimization devices to be able to automatically control the intensity of a laser light used. As an alternative or in addition thereto, it is preferable for the process and/or cost optimization devices to be designed so as to make it possible to evaluate two half frames which display different positions or views, comprising for this purpose especially a pulsed laser for exposure purposes.

Other alternative or additional embodiments of a surface mapping device according to the present invention, in particular for obtaining surface data of teeth, provide that the devices for the process and/or cost optimization comprise devices for carrying out a calibration procedure by evaluating overlap errors at matching points and/or that an image-recording device, in particular a CCD chip, is arranged so as to ensure that lines, taking into account the Scheimpflug angle, are located perpendicular to the direction of travel of the measuring table.

Another variation of a surface mapping device, in particular for obtaining surface data of teeth according to the present invention, provides that the devices for the process and/or cost optimization comprise devices for archiving especially three-dimensional data of the jaw and for modeling the bite position of the upper and lower jaws.

Special, preferably mechanical, embodiments of the surface mapping device are based on the disclosure contents of FIGS. 3 and 4 and/or 5, 6, and 7 and on the description associated with these figures.

Moreover, it is to be preferred if, in the surface mapping and generating device especially for the production of dental prostheses, the devices for the process and/or cost optimization comprise devices for an optimized preparation of at least one tooth stump for the production or placement of a dental prosthesis thereon and/or devices for taking into account the bite position of the upper and lower jaws.

The surface mapping and/or generating methods for reaching the above-mentioned objective of the present invention are characterized in that they use one or a plurality of the devices described above and function correspondingly.

Finally, the present invention also makes available a patient data archiving system which is marked by a chip card and/or decentralized data storage systems, in particular for dental data.

Certain aspects of this invention will be explained in greater detail below.

According to one aspect of the present invention, it is provided that raw material is recovered based on the surface mapping technologies, devices, and methods, such as are described in the above-mentioned publications which are hereby incorporated by reference into the present invention, hereinafter simply called "scanners" and "scanning," in combination with, for example, a milling machine. The scanner, in combination with the milling machine and a suitable electronic data processing (EDP) device, forms a CAD-CAM system, in particular for the production of dental prostheses made of gold or platinum. The recovery of raw material can be preferably implemented by providing that, for example, the milling machine used is equipped with devices, e.g., for siphoning off gold or platinum dust or chips. Considering the high cost of the raw materials, such as gold or platinum, this results advantageously in a considerable reduction of the cost for the production of dental prostheses made of gold or platinum.

According to another aspect of the present invention, the scanner technology disclosed in the publications cited above is further improved.

This is made possible, on the one hand, by an automatic control of the intensity of the laser light used. To implement this, the reflectivity, for example, of the surface of the tooth to be mapped is determined by way of the intensity of the light that is, e.g., recorded by a CCD chip. Based on the result of the determination, the intensity of the laser light is subsequently readjusted. The improvement of this embodiment is to be seen in the fact that this reduces measuring errors due to an under- or overcontrol of the measured signals. The present invention also relates to devices and methods associated with the description above.

The scanner technology of the present invention is improved, on the other hand, by an increase in speed in that, instead of a full frame consisting of two composite half frames, two such half frames which show different views are evaluated by the camera or the CCD chip. The different views are obtained by different positions of the surface, for example, of a tooth relative to the device for recording this surface (e.g. a camera with a CCD chip or a CCD chip alone).

It is possible to advantageously further develop, in particular, the improvement mentioned above and, quite generally, the scanning technology used in that the laser used is triggered by pulses, similar to a stroboscopic effect, and that, for example, the table which holds the object, the surface of which is to be mapped, such as a tooth or a model of a tooth, is, in particular, continuously moved. Because of the pulsed laser beam, snapshots or "still images" of each position of the object relative to the camera are recorded, since during the short time of exposure to a laser beam pulse, the object appears to stand still in a certain position and, in this position, can be recorded by the camera. It is to be especially preferred if each individual laser pulse is associated with the recording of a half frame.

Yet another improvement of the scanner technology according to the present invention concerns a calibrating procedure which corrects different spatial distortions of the measured quantities obtained. To implement this, a body is scanned from different angles. The measurements are assembled by means of a matching algorithm. The overlap errors which are produced at different points of the object when these measurements are assembled are analyzed so as to ensure that variations in all spatial directions are detected. These variations lead to calibration errors from which, in turn, calibration parameters can be calculated in all spatial directions and spatial rotations. In the course of subsequent measurements, these calibration parameters can then be automatically taken into consideration by the EDP unit, which advantageously contributes to an increased precision of measuring. Further details related thereto follow from the practical example shown in FIG. 1.

The prior-art scanner technology mentioned above is further improved by this invention in that a CCD chip (or, generally, a surface image recording device) is arranged so that, for example, camera lines, taking into account the Scheimpflug angle, are positioned so as to be perpendicular, e.g., to the direction of travel of the measuring table on which the object to be scanned is placed. Further details related thereto are illustrated in greater detail in the practical example shown in FIG. 2. This makes possible an improved utilization of the measuring area for scanning, for example, teeth, but it should be remembered that commercially available chips are not square.

The conventionally known scanner technology can be even further improved in that the present invention provides for the configuration of traveling and pivoting axes for the object carrier, the object and/or the camera so that it is possible to view all undercuttings present in the jaw when the invention is used, e.g., for mapping the dental surface. The advantage is that a fully automatic scanning/measuring strategy can be used.

According to another aspect of the present invention, different EDP modules are advantageously used, for example, in different fields of dental medicine.

Thus, the present invention makes available a scanner technology which comprises an EDP system, preferably in the form of a standard computer with special software as the control device, which is suitable for archiving, e.g., three-dimensional data of the jaw, in particular surface data. This archiving system serves as a substitute for previous forms of systems for archiving such data in the form of plaster models. In many areas of dental medicine, it was previously necessary to retain the plaster models of patients' teeth for a period of up to 10 years, which required an enormous space for storage. Archiving these data electronically, however, not only eliminates the need for a large storage space but also makes it possible to utilize the archived data more rapidly, more easily, and at considerably lower cost. Thus, it is possible, for example, to record and archive 3-D measuring data of previously healthy dental surfaces. As a result, years later, e.g., when a tooth needs to be replaced, the tooth can be reconstructed in the form of a dental prosthesis which, for example, can be produced by milling its surfaces on the basis of the archived data.

An electronic archiving system for jaw and/or dental data, however, provides for many other additional advantageous uses as well. Thus, these data can be processed by means of a suitable EDP system to model the original bite position of the upper and the lower jaws. In particular, this can be accomplished by first scanning the lower jaw, by subsequently placing a check bite (impression in the patient's mouth while he or she bites down) on the lower jaw, and by scanning it again. Thus, both dental surfaces in the bite situation are recorded. Both data records can be viewed separately or in combination with each other, and all dental analyses associated therewith can be carried out, for example, qualitatively or quantitatively (in the form of distance or volume measurements). To complete the measurement, the entire upper jaw can be scanned and spatially referenced by means of the check bite and, for example, matching software. Furthermore, it is possible to also simulate masticatory motions on the computer by means of recording the movement of the jaw and the bite check. Referencing the measured data of the upper and the lower jaws can also be used to modulate dental prostheses in connection with the CAD-CAM technology.

An additional variation of the present invention relates to a scanner technology which comprises an EDP system, such as a standard computer with a suitable type of software as the control device, with which the bite position of the upper and lower jaws can be modeled particularly for orthodontic surgery. The treatment plan, for example, for installing a dental brace, can be simulated in that, for example, in the software, the teeth are divided into dental groups, down even to individual teeth. Such groups and/or individual teeth can be moved and the final positions can be simulated. This provides answers to questions, such as whether there is enough room on the alveolar ridge and how the bite will look after the treatment. The treatment can be controlled by means of other EDP and software systems which can be modularly combined. At certain intervals, a jaw can be rescanned again and again. The successive chronological images can subsequently be shown as an interpolated "film." This makes it possible to compare the progress of the actual treatment with the planned treatment and to identify and carry out corrections. Furthermore, these series of images can be archived and can, for example, be used as evidence in cases of law suits. In addition, these images also facilitate and expedite the communication with expert witnesses and insurance companies.

Another aspect of the present invention is related to a scanner technology which comprises an EDP system and an electronic control (for example, by means of software) so as to be able to model, e.g., the bite position of the upper and the lower jaws particularly for orthodontic surgery. This aspect of the present invention makes it possible, in particular, to incorporate the measured data of the jaw bones (determined, e.g., by means of computed tomography) using a suitable matching software. The planned treatment (e.g., an operation of the jaw) is simulated in that, for example, in a software, the teeth, the jaw, and the jaw bone are divided into groups of tooth and jaw sections (down to individual teeth). The groups and/or individual teeth can be moved and the final positions can be simulated. This makes it possible to answer questions, such as whether the space required is in fact present and how the patient will look after the treatment. In this case, another EDP and software module can be used for follow-up treatment. At certain intervals, each respective current status is scanned. The images taken over time can be displayed in the form of an interpolated "film." The progress of the actual treatment can be compared to the planned treatment, and based on this comparison, potentially required corrections can be made. This aspect of the present invention makes it possible to advantageously plan and simulate implants. Among the other benefits worth mentioning is the fact that series of archived images can be used as evidence in cases of potential law suits and that the communication with expert witnesses and insurance companies is made easier and faster.

The scope of the present invention also extends to a patient data carrier, such as a chip card, which contains all data relating to a person's health and illnesses. Such an individual data carrier can be integrated into an administrative and archiving system which comprises, in particular, decentralized storage systems for archiving large quantities of data which can be accessed by means of accessing means on the data carrier. Thus, it is possible to archive and make readily available, for example, basic dental patient data which can include the 3-D data of the jaw and individual teeth and their dental surfaces as well as internal structures of individual teeth and data on the production of dental prostheses used (data on material and, e.g., milling). In addition, data on health insurance, digital X-rays, formerly and presently attending physicians, and, in general, the entire patient history can be stored on said data carrier. The scope of the present invention also extends to special reading and evaluating units which may also be integrated into the system. Thus, among the advantages obtained are double archiving for patients, improved retrospective follow-up means for insurance companies, and the availability of data even if the patient changes his or her address.

Furthermore, the subject matter of the present invention also relates to another variation or embodiment which allows for the implementation of a pulsed measurement, the basic principle of which had already been mentioned earlier.

A suitable surface mapping device or system comprises, for example, a linear table, a CCD camera, a frame grabber card, and a laser line module. To obtain the data, the laser line is projected continuously on the object to be measured. The measuring table moves the object step by step through the measuring arrangement (laser line and CCD chip). After each step, a measurement is carried out.

The method was previously carried out as follows: The measuring table moves into a starting position and stops. The object must be at rest to ensure that the picture taken is not "blurred," which can lead to imprecise measurements. Subsequently, the CCD camera reads out a line (full frame) and transmits the signal to the frame grabber card. Next, the table is accelerated (approach ramp). Then the table is slowed down and stopped in a predetermined position (braking ramp). The CCD camera now reads out the next line. This entire process takes place in complete darkness. The laser diode can be regulated only to a specific output to ensure that the signal is not overcontrolled.

The novelty of the present invention is that the laser line is projected in a stroboscope-like fashion onto the object to be measured, which means that light flashes in the form of a laser line are projected at regular intervals onto the object. The measuring table moves the object continuously through the measuring arrangement (laser line, CCD chip). With each light flash, a measurement is simultaneously carried out. In particular, the measuring table moves at a controlled/supervised speed which is adjusted to the flash control. At preferably regular intervals (time or travel path of the table), a flash is emitted, and at the same time, a half frame of the CCD chip is read out. This signal is transmitted to the frame grabber card and evaluated by means of special software. The flash time is so short that any "blur" potentially caused by the continuous movement of the table is negligible.

As a result of the embodiment of the invention just mentioned, the measuring process is accelerated by a factor of 5 since the approach and braking times of the table are eliminated and the light flashes can be timed fast enough so that the readout can take place with half frames. An additional advantage is that the control device can have a less expensive design since only a uniform advance is required and no precise resting position has to be set. Another advantage is that the optomechanical configurations formerly used can continue to be used since the novelty exists or can be implemented with regard to the open-loop control, the closed-loop control, and the software for the components. Another advantage is that the intensity of the flash used is considerably higher than the formerly used laser signal, as a result of which it is possible to carry out the measurement even in daylight, without having to darken the measurement room, which considerably reduces the labor and time expenditure especially when exchanging objects to be measured.

In addition to the technical specifications for the "stroboscopic laser," etc., already described above, the scope of the present invention also extends to mechanical designs which are considered worth protecting or capable of protection, both as far as the underlying concept is concerned and as to the actual embodiments and operating procedures in combination with each other or each by itself.

Especially when compared to the prior-art device for the production of a dental prosthesis according to European Patent EP 98115809.0, the present invention is marked by a number of concepts and designs which dramatically reduce the cost of producing such a device and make it function more reliably. In addition, these aspects of the present invention constitute advantageous and preferred further developments and combinations of the technology disclosed in German Patents DE 44 39 307 A1 and DE 197 21 688 A1, the entire contents of which as well as the contents of the European Patent Application EP 98115809.0 are hereby fully incorporated by reference into the present documents to avoid mere identical repetitions. In particular, the individual characteristics and combinations of characteristics can, but need not necessarily or exclusively be, combined with the stroboscopic technique described above.

With the individual aspects of the present invention, above all, technical improvements over and above the technical teaching in EP 98115809.0 are made available, with these improvements being specific, without being restrictive.

Other preferred and advantageous embodiments of the present invention follow from the individual claims and combination of such claims.

Below, the present invention will be explained in greater detail only by way of practical preferred embodiments with reference to the drawings, with these embodiments being no more than possible examples.

BRIEF DESCRIPTION OF THE FIGURES OF THE DRAWING

As can be seen:

FIG. 1a shows a diagrammatic top view of a jaw in which prior-art scanning lines are sketched in;

FIG. 1b shows a diagrammatic front view of a jaw in which the scanning lines according to FIG. 1a are sketched in;

FIG. 1c shows a diagrammatic top view of a jaw in which scanning lines according to the present invention are sketched in, FIG. 1d shows a diagrammatic front view of a jaw in which the scanning lines according to FIG. 1c are sketched in;

FIG. 2b shows a diagrammatic view of the object to be measured of FIG. 2a in which prior-art scanning lines are sketched in;

FIG. 2d shows a diagrammatic view of the object to be measured of FIG. 2a in which the scanning lines according to the invention are sketched in;

DETAILED DESCRIPTION OF PREFERRED EMBODIMENTS OF THE INVENTION

In the figures, identical or similar parts or identically or similarly functioning parts have the same reference numbers or are depicted in a comparable manner so that a person skilled in the art is able to recognize parts and their combinations, functions, and modes of actions possibly solely by looking at the figures, by comparing said figures and/or by reading the description below even if no reference is expressly made or shown between the individual figures and/or between the figures and the text.

First, a conventional measuring method will be explained so as to provide insight into the functioning of the device involved. This type of measuring method is used, for example, by the firm of DCS Forschungs- und Entwicklungs AG in Allschwil, Switzerland, and has been introduced to the public as early as in 1999. This measuring method has been considerably improved by the present invention.

FIGS. 1 and 2 show a top view and a front view, respectively, in which jaw K is being scanned. For example, five measuring lines S1, S2, S3, S4, and S5, one next to the other, are scanned. The five measuring lines S1 to S5 overlap in areas B which are hatched in FIG. 1a and omitted for the sake of clarity in FIG. 1b. FIG. 1b serves only to illustrate the position of measuring lines S1 to S5 in the front view of jaw K and to show the direction of the scanning radiation which is denoted by arrows P. Overlapping regions B make it possible to assemble the data of the individual measuring lines by means of matching methods so as to form an overall image of jaw K.

Figure 1A:
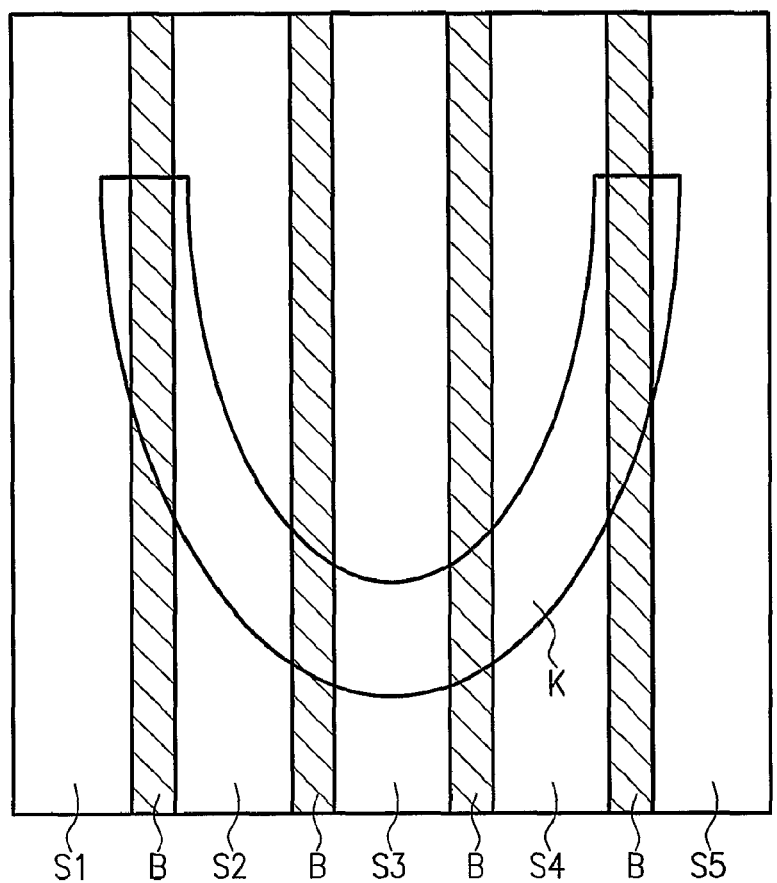
Figure 1B:
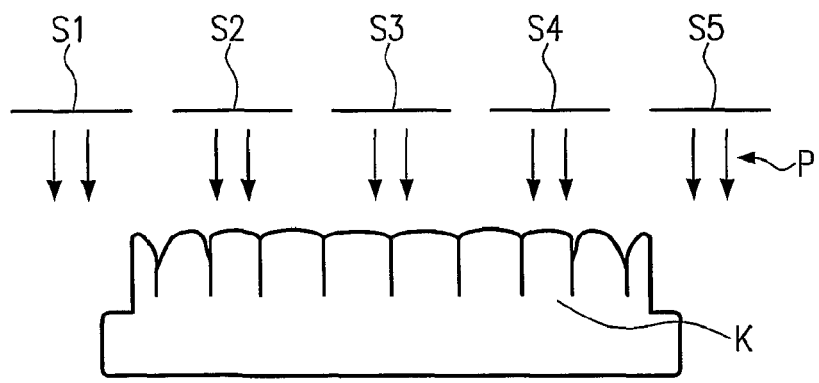
Figure 1C:
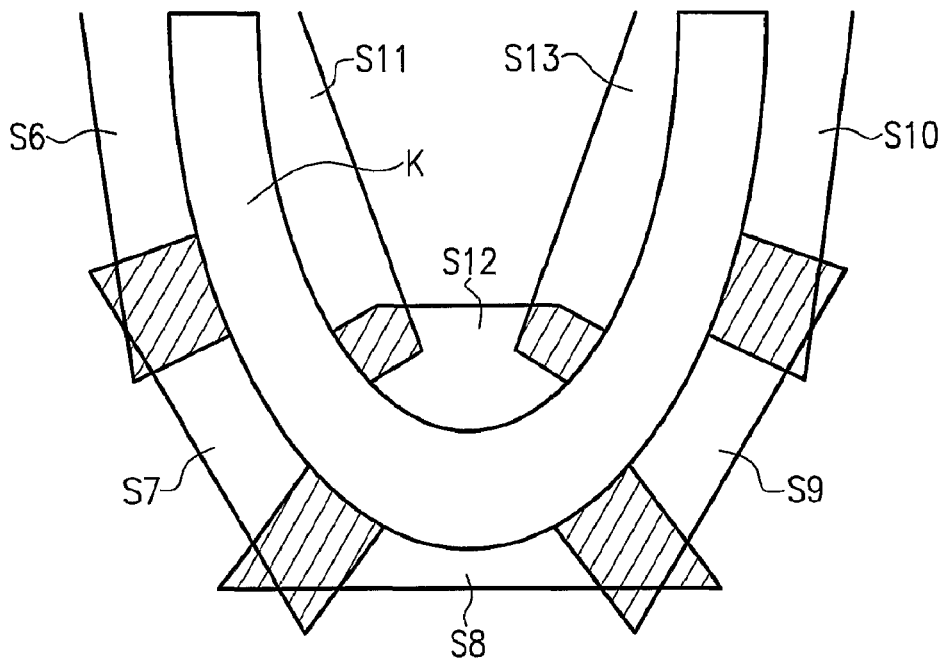
Figure 1D:
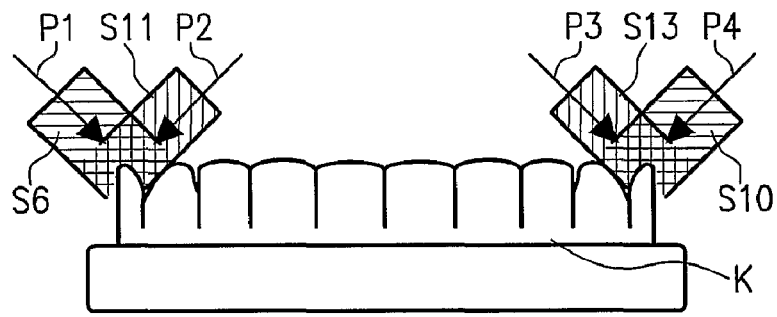

FIGS. 1c and 1d, again shown as a top view and a front view, respectively, illustrate a variation of the prior technology described above based on the present invention. According to this method and using the appropriate devices, measuring lines S6, S7, S8, S9, S10, S11, S12, and S13 are generated, except that these lines are made up only of so-called half frames, so that, although the number of measuring lines is greater than in the variation according to FIGS. 1a and 1b, these measuring stripes are able to function with markedly fewer data. The position of measuring lines S6 through S13 is shown in the top view of FIG. 1c relative to jaw K. In FIG. 1d, the directions of the radiation are diagrammatically denoted by arrows P1, P2, P3, and P4, using measuring lines S6, S11, S13, and S10 as an example. In FIG. 1c, overlapping areas B of the neighboring measuring lines are again shown in hatched representation. Because of the directions of radiation which differ from prior art for the individual measuring lines, the data obtained for jaw K are more precise, with the number of data and the amount of processing required being reduced with respect to prior art since only half frames are used.

Figure 2A:
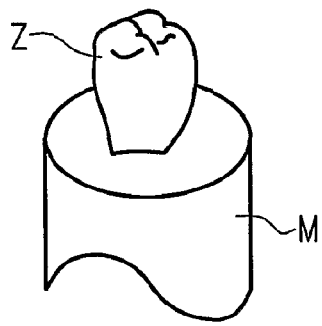
FIG. 2a shows a diagrammatic perspective view of an object to be measured in the form of a tooth.

In FIG. 2a, one single object to be measured in the form of a tooth Z is diagrammatically shown in a perspective view after placement in measuring pot M which, for this purpose, is filled, for example, with a modeling material into which the lower end of tooth Z is inserted (not shown).

Figure 2B:
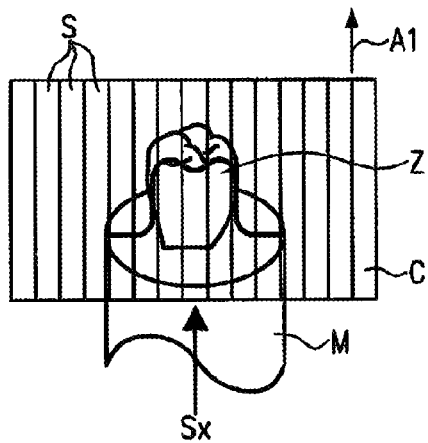
Figure 2C:
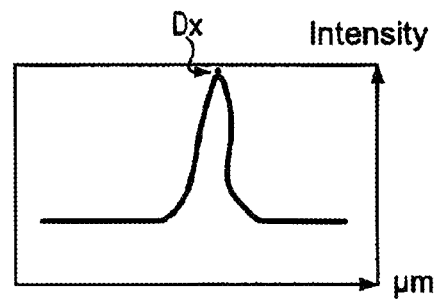
FIG. 2c shows a diagrammatic view of a signal image of a scanning line of FIG. 2b.

For this object Z to be measured, the position of the measuring lines S is diagrammatically shown in FIG. 2B, and FIG. 2c shows the signal image for one measuring line Sz in which only one measuring point Dx is obtained. In FIG. 2b, the readout direction (line direction) is additionally denoted by arrow A1. The sum of all measuring lines S forms the area of chip C as the image mapping device which can be, for example, a CCD chip or any other camera system.

Figure 2D:
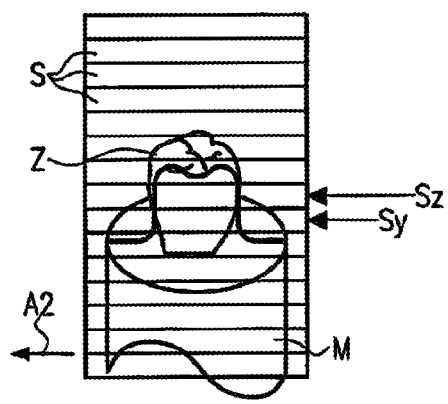
Figure 2E:
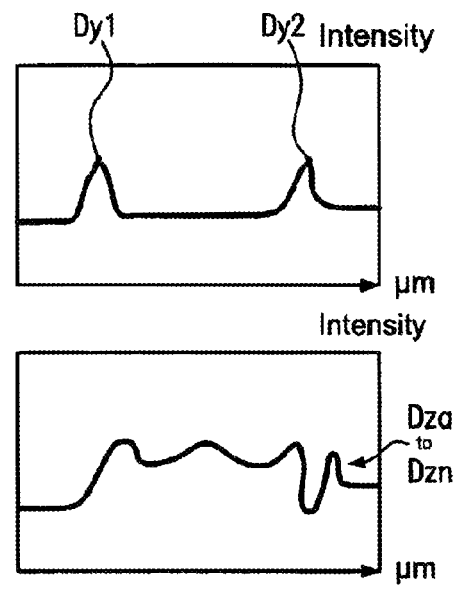
FIG. 2e shows a diagrammatic view of a signal image of a scanning line of FIG. 2d.

In contrast, a measuring line S according to the present invention produces a plurality of measuring points, e.g., Dy1 and Dy2 or Dza to Dzn, as illustrated in FIGS. 2d and 2e, which figures are representations corresponding to those in FIGS. 2b and 2c. The readout direction in FIG. 2d is indicated by arrow A2, and chip C and the position of measuring lines S are thus rotated by 90° relative to prior art. This configuration according to the present invention produces two measuring points Dy1 and Dy2 in measuring line Sy. And the measurement in line Sz produces even a plurality of measuring points Dza to Dzn. For the purpose of the subsequent evaluation, the chip configuration is preferably extrapolated and simulated by means of suitable software in the same manner as in prior art (see FIG. 2b). Per line, the readout direction which is again obtained in the same manner as in prior art, however, again contains several measuring points which can be computed first as point 1, subsequently as point 2, etc. Thus, although the amount of work required is reduced as a result of the fact that only half frames are used, this aspect of the invention leads to a greater number of data, which further increases the precision of this invention relative to prior art.

Figure 3:
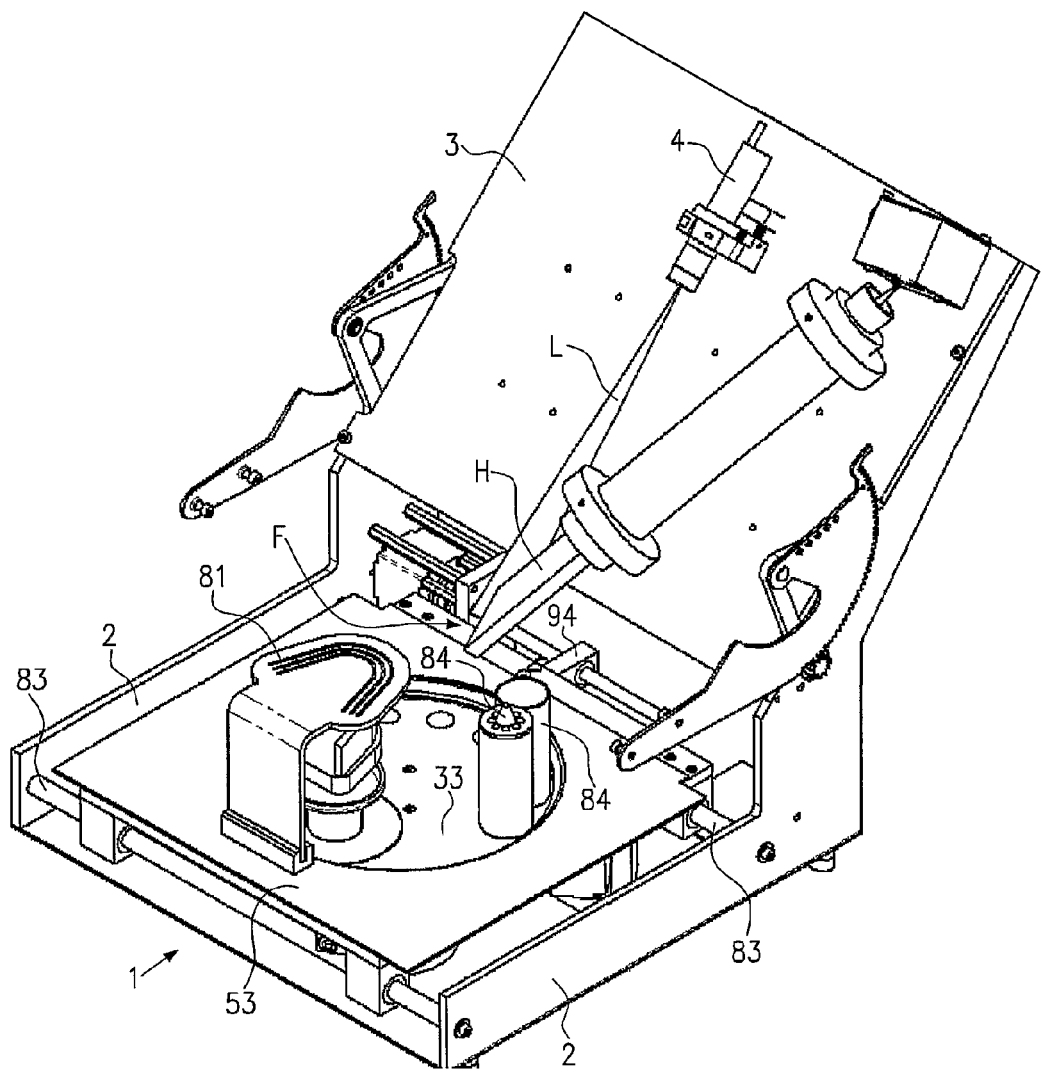
FIG. 3 shows a perspective diagrammatic view of a practical example of a surface mapping device from an oblique angle from above.
Figure 4:
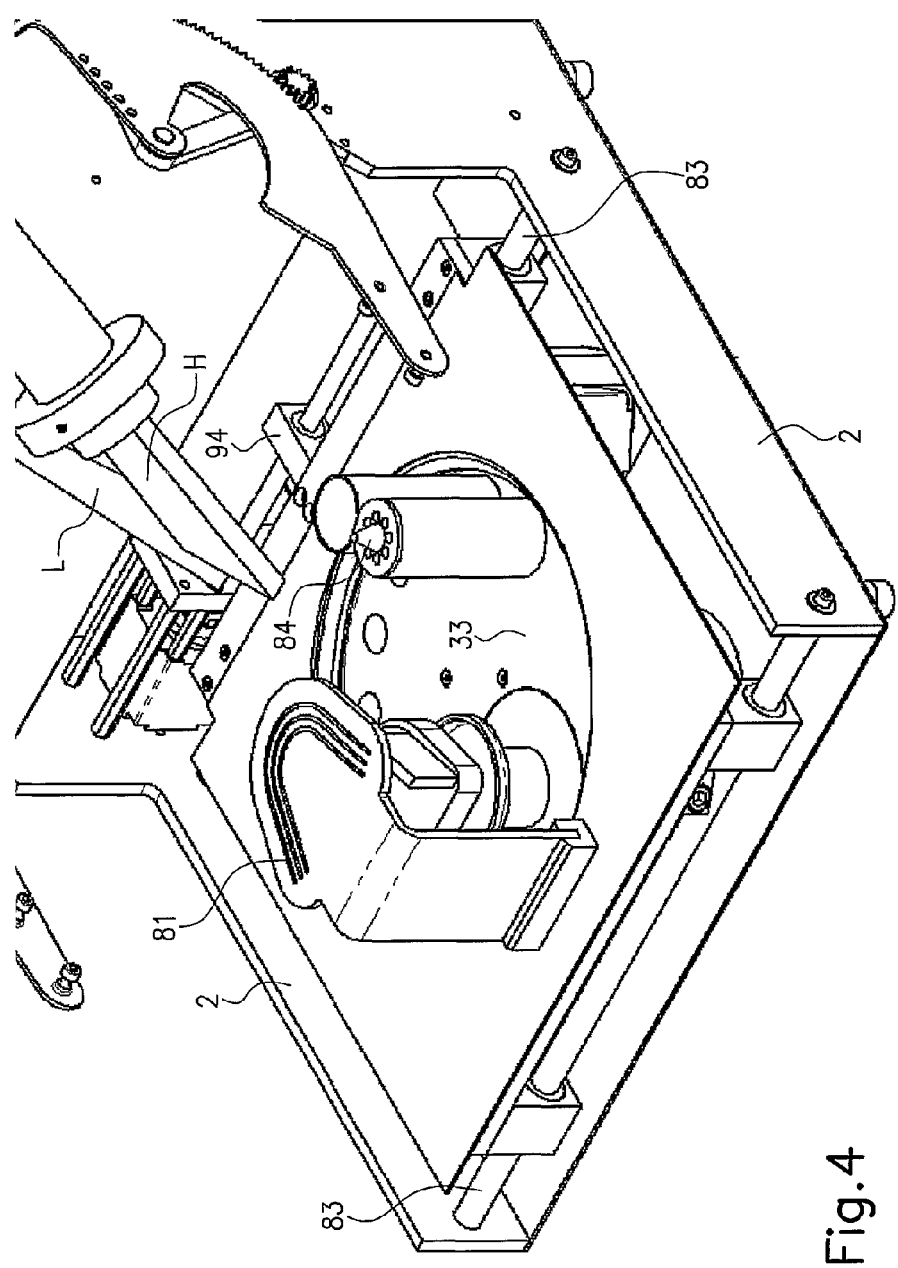
FIG. 4 is an enlarged representation of one portion of FIG. 3.

FIGS. 3 and 4 which are enlarged representations of a portion of FIG. 3 illustrate surface mapping device 1 with laser optics 4 from which laser line beam L exits. The point of intersection of laser line beam L with the rectangular image field F which exits from the lens defines measuring field F. Each object to be scanned must be passed through this measuring field F. This also applies to the embodiments according to FIGS. 5, 6, and 7 although this particular detail is not shown in these figures which concentrate on the other features. Thus, to avoid repetitions, this aspect will not be mentioned again in the following discussion of FIGS. 5, 6, and 7; however, the use of this technology is deemed to be obvious to the person skilled in the art who will know where and how to use it.

Figure 5:
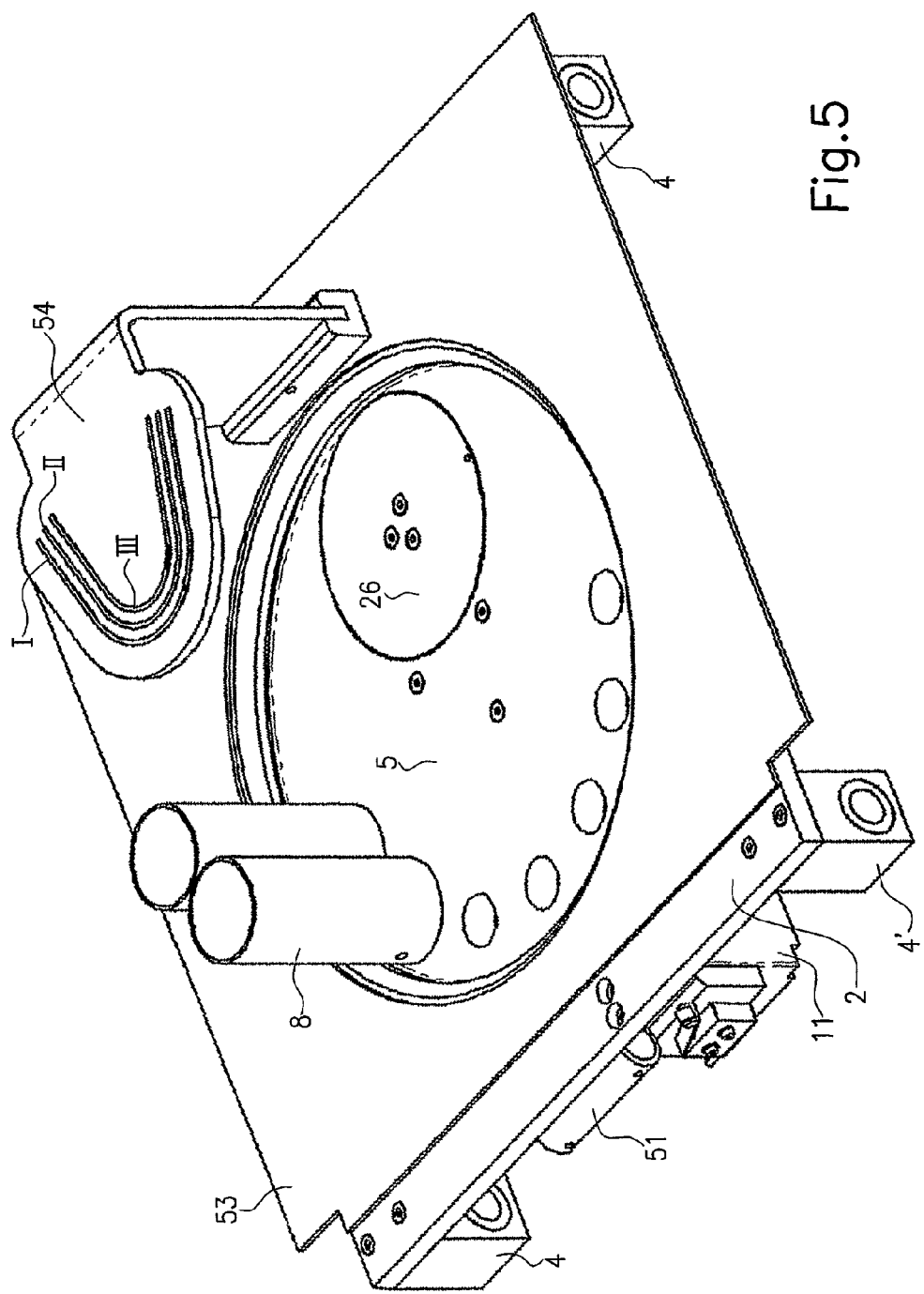
FIG. 5 shows a perspective diagrammatic view of the practical example of the enlarged surface mapping device of FIG. 3 from an oblique angle from above in a different setting.
Figure 6:
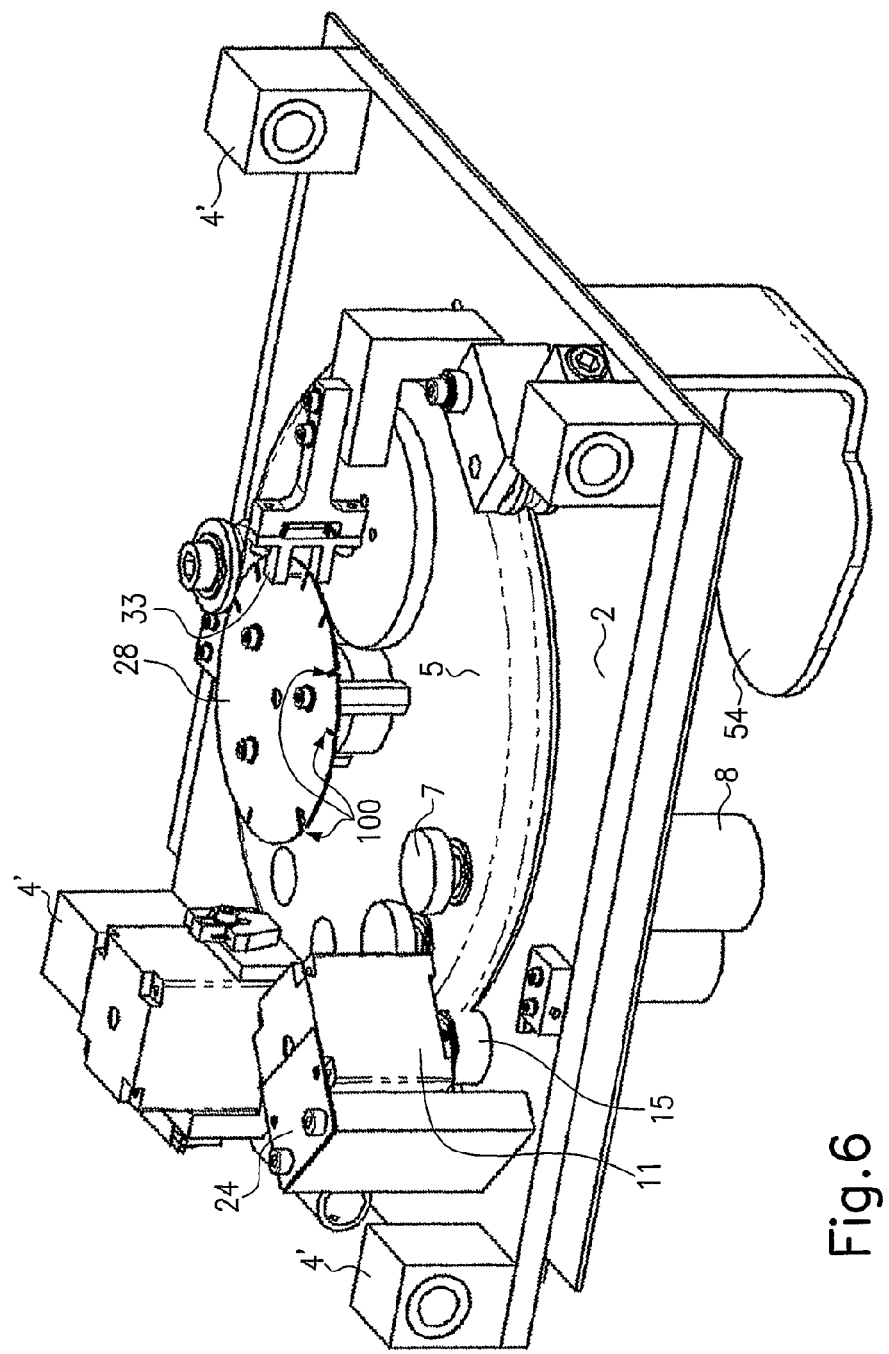
FIG. 6 shows a perspective diagrammatic view of the practical example of the enlarged surface mapping device of FIG. 3 from an oblique angle from below.
Figure 7:
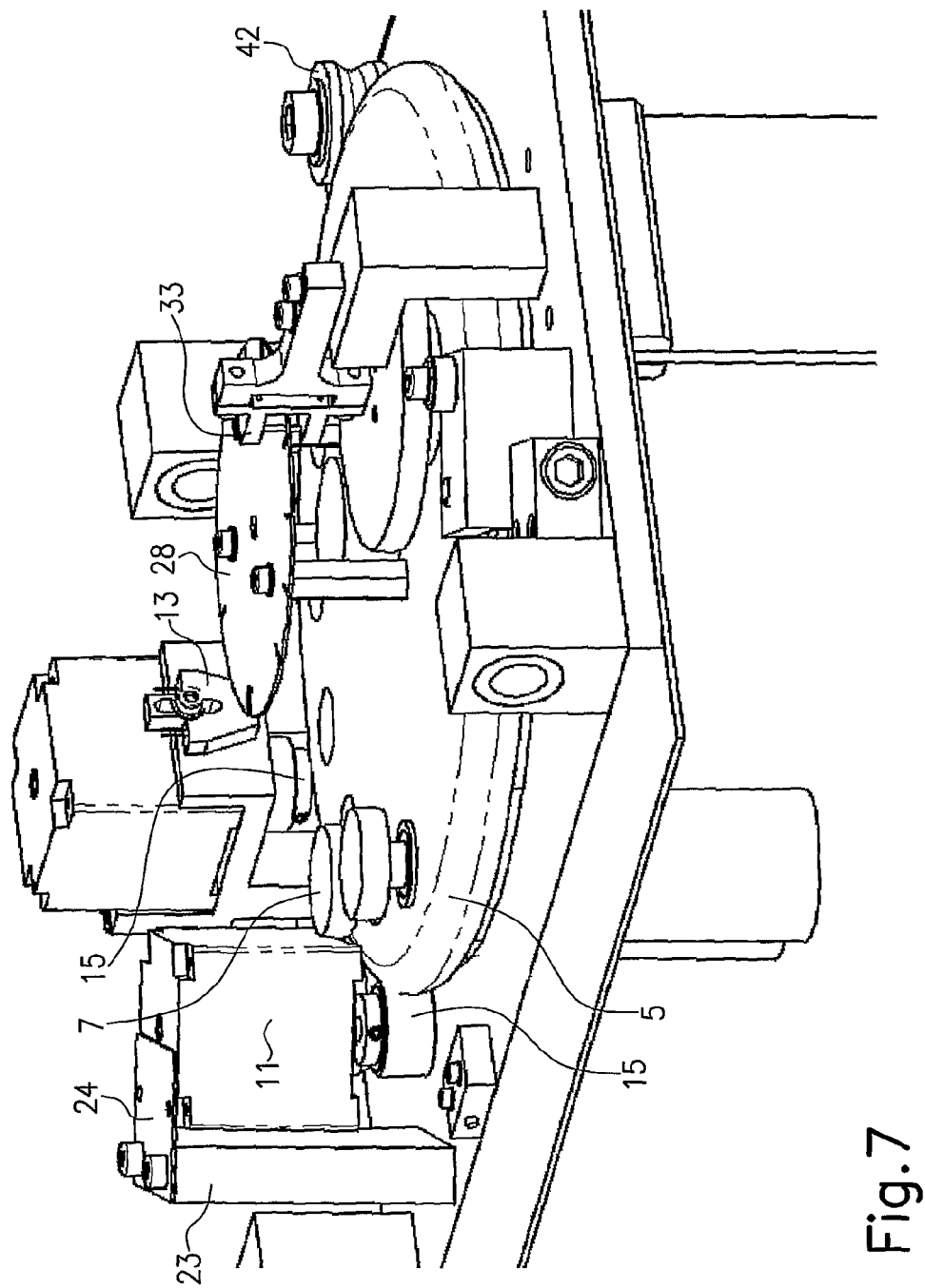
FIG. 7 shows a perspective diagrammatic view of the practical example of the enlarged surface mapping device of FIG. 3 from an oblique angle from below, the device having been slightly rotated relative to the view shown in FIG. 6.

To avoid repetitions, the following discussion will by reference also include FIGS. 5, 6, and 7 to the extent that the design is identical or comparable.

The "passage through" measuring field F is implemented by means of a linear guide 83 (or reference number 4' in FIGS. 5 and 6). To be able to position a plurality of individual objects, such as, in particular, teeth, within the measuring field, a rotating plate 33 (or reference number 5 in FIGS. 5, 6, and 7) rotates from measuring pot 84 to measuring pot 84 (in FIG. 5, the measuring pots are denoted by reference number 8). In FIG. 3, only two measuring pots 84 are sketched in by way of an example (the same applies to FIG. 5, e.g., where only two measuring pots 8 are shown), but a total of, for example, seven measuring pots could be mounted.

Once a measuring pot 84 (or 8 in FIG. 5) holding a tooth arrives in the measuring field, the large rotating plate 33 (or 5 in FIGS. 5, 6, and 7) stops rotating. Thus, rotating plate 33 (or 5 in FIGS. 5, 6, and 7) only serves to position the pots 84 (or 8 in FIG. 5) holding the individual teeth and/or a jaw, which will be explained in greater detail below. As already explained above, the measurement as such is carried out by means of a linear movement of measuring table 53 on the linear guide mounts 83 or 4' (FIG. 5).

This produces a measuring line which can see only one side of the tooth to be scanned. To be able to obtain additional measuring lines from additional angles, pot 84 (or 8 in FIG. 5) located in the measuring field can be rotated around its own axis between the individual measurement. This can lead, for example, to eight images, or, in other words, pot 84 (or 8 in FIG. 5) is rotated by 45° around its own axis between the measurements. Thus, in such a case, eight measuring lines from different angles are obtained. Portions of the thus obtained surface data appear in several measuring lines. By means of these overlapping areas, suitable devices or methods in the form, for example, of an already discussed matching software can assemble the individual measuring lines to form a complete 3-D surface image of a single tooth, thus ensuring a high precision of measurement.

These data now make it possible to mill the inside data record of a dental crown. In addition to milling individual crowns, several single teeth can also be combined to form a bridge. To be able to mill bridges, the spatial position of several single crowns relative to one another must be determined as fast as possible. For this purpose, a complete jaw model is scanned in the same way as a single tooth. It is placed on an additional rotating plate 26 which is provided in rotating plate 5 of FIG. 5.

Figure 8:
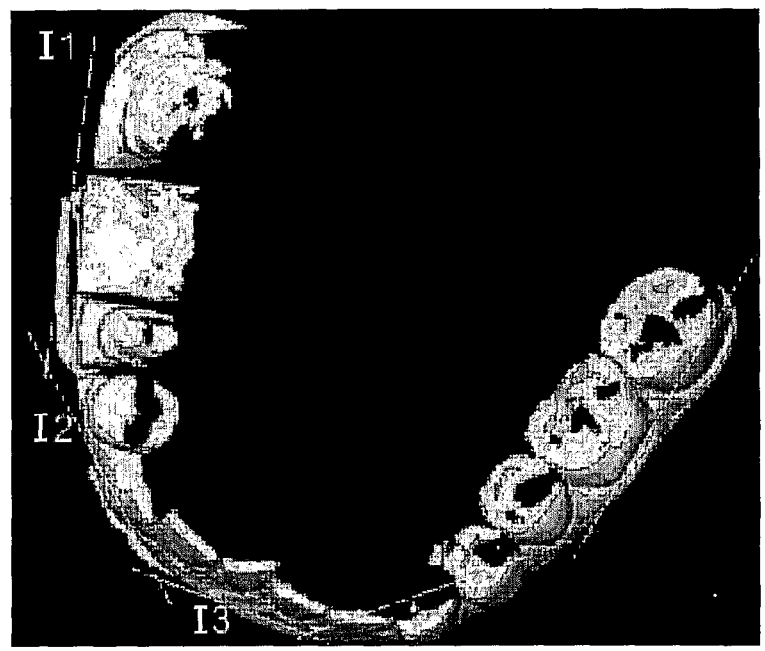
FIG. 8 is a graphic representation of a jaw with diagrammatically sketched-in positions of measuring lines on the basis of data that were scanned in according to the present invention.

The result can be seen in the image of FIG. 8 (the direction of the measuring lines is illustrated by five white lines (some of which, by way of an example, are denoted by I1, I2, and I3 while the others are simply sketched in as lines). Although this result of the measurement does not include all data of the jaw, sufficient data for the outer surfaces are available so as to be able to automatically produce these structures with the data of the individual dental stumps.

Figure 9:
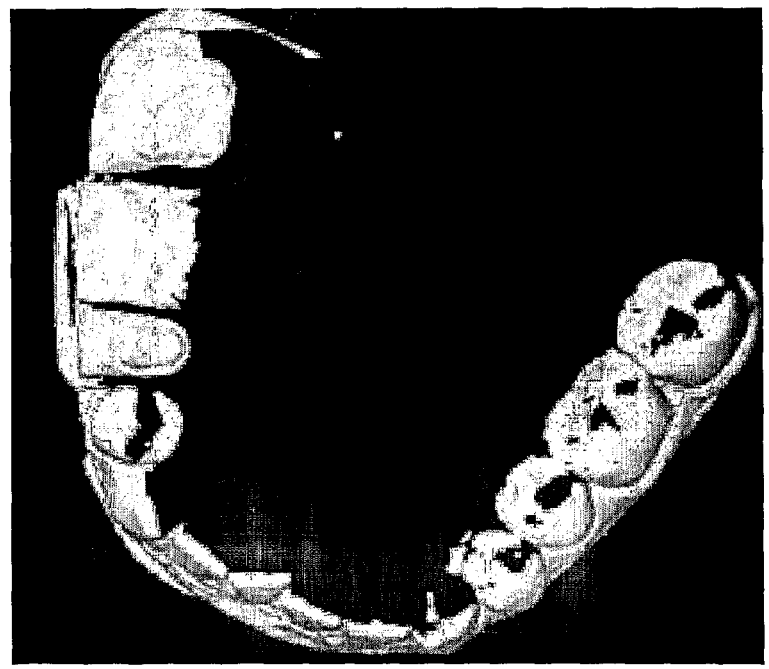
FIG. 9 is a graphic representation of the jaw with teeth of FIG. 8 treated according to the present invention.

Subsequently, suitable devices or processes are used to start a software search which leads to an agreement of the data. The result can be seen in the image of FIG. 9. The two highlighted data records [sic] of the first tooth at the top of the left side and of the next tooth in the jaw model following the gap represent the referenced single teeth.

Below, additional improvements will be illustrated and explained.

With reference to FIGS. 5, 6, and 7, with FIG. 5 being a perspective top view and FIGS. 6 and 7 being perspective views of the same device from below, a rotating plate 5 serves to transport a number of measuring pots 8 for single teeth for placement under the laser measuring setup (compare FIG. 3). This rotating plate 5 is driven by means of a friction wheel 15 (see FIG. 6). The front of this friction wheel 15 is pressed against rotating plate 5 by means of a spring plate 24 (see FIG. 6). This compensates for the potential wear of a rubber surface or of the rubber material of friction wheel 15.

The position of rotating plate 5 is determined by means of encoder disk 28. In the case at hand, the disk is designed in the form of a plate 28 (see FIG. 6) which has slots 100 precisely in those regions in which the required stop positions are located. Slots 100 are detected by means of a light barrier 33 (see FIG. 6). In a suitable device or by means of a feature that is incorporated into the process, a control software evaluates the light barrier signals and starts and stops the table or plate 5. Rotating plate 5 has seven positions/pots for single teeth. If more than seven preparations/teeth are to be worked on (a maximum of 14 teeth per jaw is possible), the work can be carried out in 2 batches.

Advantages of the devices described above:
extremely favorable production cost, available anywhere
no wear and tear
balance quality which ensures a quiet operation
exact knowledge of the positions As an alternative to friction wheel 15, it is also possible to use, for example, a belt pulley or a toothed belt.

As to the prior art, reference is hereby made to a scanner of the firm of DCS Forschungs-und Entwicklungs AG in Allschwil, Switzerland, which was first presented to the public at the 1999 IDS exhibit in Cologne.

In the prior art, rotating plate 5 which was toothed along its outer periphery was used for the same purpose. The plate was driven by means of a small toothed wheel made of plastic. The path segments/angles of rotation were traversed by means of a number of steps which were predetermined in the software. A feedback to the control to determine whether the angle was in fact maintained did not exist. The plate was able to hold 14 pots which made it possible to scan a maximum of 14 stumps per jaw within one scan. This prior-art technology has the following drawbacks:
teeth along the outer periphery make the plate expensive and not readily available
the small plastic toothed wheel was subjected to considerable wear
high noise level during operation
lack of feedback regarding the position along the path
the 14 pots required (instead of preferably seven pots provided by this invention) are responsible for disproportionately high costs in the improbable case that there are more than seven connected dental stumps in one procedure; moreover, the 14 pots require a lot of space and determine the size and weight.

The cost of the construction of the frame can be further reduced by additional measures. Thus, the frame of the apparatus/device is suspended from two guide rods 83 (compare FIGS. 3 and 4). Thus, the complete frame of the apparatus comprises only two lateral parts 2 (compare FIGS. 3 and 4), the guide rods 83 (compare FIGS. 3 and 4), and an optical plate (FIG. 5). Inaccuracies potentially caused by the mechanical design of the linear rod guide are compensated for by the software (e.g., by means of so-called "look-up tables"). A precision spindle 94 (compare FIGS. 3 and 4) is attached to the side of the moving table on which the laser setup is located. Thus, errors in the angle of the spindle have a lesser effect. Advantages of this setup include low production costs, high precision, a markedly lower transport weight, and a more compact design.

As to the design mentioned above, ground linear guides with ball cages instead of 2 linear rod guides were used in the device produced by the firm of DCS Forschungs- und Entwicklungs AG in Allschwil, Switzerland. This necessitated a massive 8-part frame construction of massive metal plates which had to be produced with high precision. For reasons of space, it had been possible to attach the drive spindle only on the side of the moving table that was located opposite to the laser, which, given the free motion of the spindle, leads to errors in the angle.

The prior art device can be further improved by providing the laser diode with protection against electric shock. For this purpose, the laser optics, the laser diode, and the electronic control for the laser diode are housed together in a metal housing. The advantage is improved protection of the diode, in particular against electrostatic charges from the outside, and the fact that the exchange of parts is facilitated in cases of needed repairs.

In the known prior-art device of the firm of DCS Forschungs- und Entwicklungs AG, Allschwil, Switzerland, the electronic components and the diode are located in separate areas. After the housing of the device is removed, both components lie bare so that the service personnel can touch these parts and thus damage the optical system.

In addition, other improvements compared to prior art are possible in the manner in which jaw models are adjusted. To be able to optimally adjust jaw models that are to be scanned, a template 54 (see FIG. 5) is needed. Since jaw models have different diameters (e.g., for children and adults), the jaw model must be adjusted to the size required. For this purpose, for example, 3 different adjustment contours I, II, and II are engraved or otherwise suitably placed on the transparent Plexiglas disk from which template 54 is preferably made.

Furthermore, other improvements are possible, for example, by rotating the individual pots by 45°. Rotating plate 5 (FIGS. 5, 6, and 7) transports individual pots 8 to the measuring position just in front of the friction wheel 15. While rotating plate 5 moves, the friction contact between the pot 8 and the friction wheel 15 is automatically generated. The novelty is that friction wheel 15 is made of rubber or at least has a rubber bearing surface while the counterwheel 7 is made of solid metal. Advantages include a reduction in price, easier manufacture, and longer life. The prior-art device manufactured by the firm of DCS Forschungs- und Entwicklungs AG, Allschwil, Switzerland, had a friction wheel made of metal while all counterwheels were covered with O rings made of rubber. The disadvantage of such an arrangement is that the O rings wear out after a certain length of time and that the production cost is high.

Another aspect of the present invention will be explained by reference to FIG. 10. This figure shows 3 dental stumps 101, each comprising a ground portion 101*a* and a residual tooth portion 101*b*. The grinding is done manually by a dentist and necessarily leads to undercuttings 102 which, when looking at several adjacently positioned individual teeth or their stumps 101, differ as to shape, position, and size. To construct a planned prosthesis 103, the overall contour of which is shown as a broken line by way of an example only on stump 101 completely on the left side of FIG. 10, on dental stumps 101, a so-called cap 104 is first produced for at least one stump 101, which cap can, as a rule, be slipped over stump 101 in exactly one slip-on or clip-on direction as indicated by arrow E. In this manner, it is not possible for cap 104 to fill the undercuttings 102 since otherwise it would no longer be possible for the cap to be slipped on. In the case demonstrated in connection with the preceding practical example, 3 stumps are located side by side, and the 3 caps 104 thereon are combined to form a bridge by connecting each adjacent cap 104 by means of a joint 105.

Figure 10:
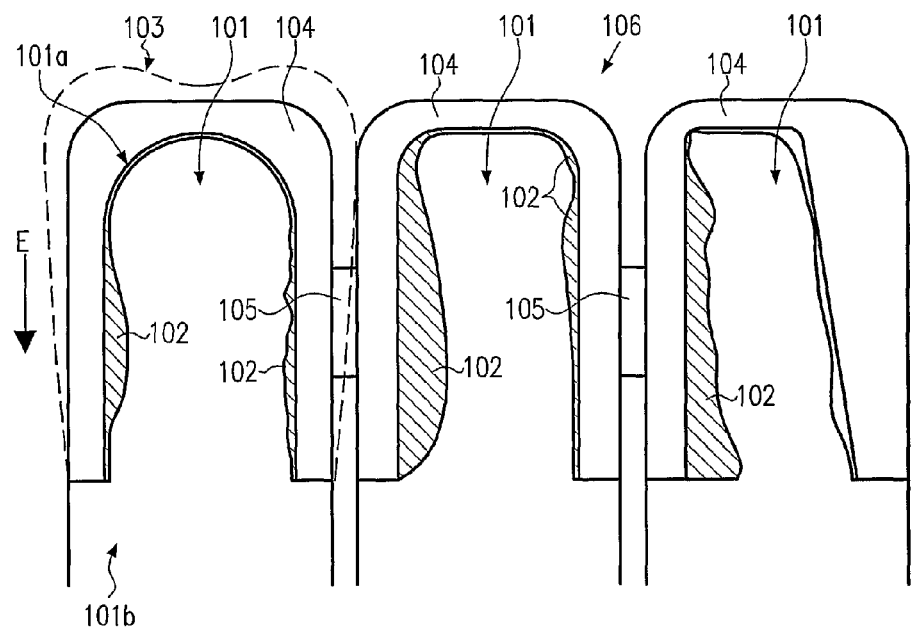
FIG. 10 is a diagrammatic partial view of a jaw in which another aspect of the present invention is illustrated.

To shape the totality of all of caps 104, it is necessary to determine an optimum slip-on or clip-on direction which minimizes undercuttings 102 which form, among other things, for example, because of the oblique position of one stump 101 relative to the other stumps 101, as is illustrated by stump 101 on the right side of FIG. 10.

This can be carried out in advance on the basis of the 3-D data obtained from stumps 101. For this purpose, as already explained in detail in the present documents, a 3-D data record is generated by means of scanning as disclosed by the present invention and used for model calculations to identify the optimum slip-on or clip-on direction. For this aspect of the method according to the present invention, different clip-on directions are successively used as a basis, and the "dead space" caused by undercuttings 102 is determined for each of the results. The optimum slip-on direction A is obtained by identifying the variation with the smallest "dead space."

Especially as a result of an oblique position of a remaining stump 101, but also as a result of other imprecisions caused during the work by the dentist, it is possible for cases to arise in which a cap, relative to a residual tooth region 101*b*, would, in certain places, have to have a wall thickness of 0 mm. In such a case, it is principally not possible to produce a dental prosthesis. Before anything else can be done, time- and cost-intensive work must first be carried out on the tooth stump 101 involved, and often it is not certain that this work will lead to a useful result.

In addition to the optimization of the slip-on direction E to minimize the undercuttings or "dead spaces" 102 as provided by the present invention, the present invention can be used to further improve the approach to the production of dental prostheses. By means of the recorded (scanned) 3-D data, it is possible to prepare recommendations for the treating dentist which tell him what kind of work should be done on the dental stumps that would more likely lead to an improvement of the fit and stability of the prosthesis to be manufactured, including what to do to markedly reduce the undercuttings or the "dead spaces" 102. For this purpose, the scope of the method according to the present invention is extended so that relative to a recorded 3-D data record of one dental stump 101 or a combination of several dental stumps 101, an optimum clip-on direction for cap 104, in particular a combination of a plurality of caps 104 to form a bridge 106, is calculated provided that changes in the shape of the dental stump/the dental stumps 101 are possible. Thus, the method and system according to the present invention serve not only to make possible an adjustment to a given situation when caps 104 or bridges 106 are produced and clipped on but also to change a given situation so as to optimize the result, i.e., the prosthesis. For example, the method and system can make provision for the inclusion of a graphic display of the stumps, including, for example, specially dyed regions, for the finishing work, which display can serve as a basis for a dialogue between a dental lab and a dentist.

Furthermore, the invention in all of its embodiments described above also has the advantage of creating the possibility of a quality assurance, including, in particular, the possibility of unambiguously connecting given treatment results with the dentist who prepared the dental stumps by means of grinding or with the dental lab which produced the caps/crowns/bridges. Thus, it will be possible for the first time to settle questions of who bears the responsibility in cases of an inaccurate fit. Furthermore, it will be possible to advantageously make use of the fact that all data at the outset of a treatment as well as all data of the dental status at certain intervals can be continuously archived in an especially simple and at all times readily accessible manner.

The method and its variations explained above by reference to FIG. 10 are equivalent to appropriately designed devices by means of which these methods can be carried out so that any devices, with which the person skilled in the art would be immediately familiar on the basis of the representation of the methods in their general and specific embodiments, are deemed to have been disclosed in the present documents.

Figures 11, 12:
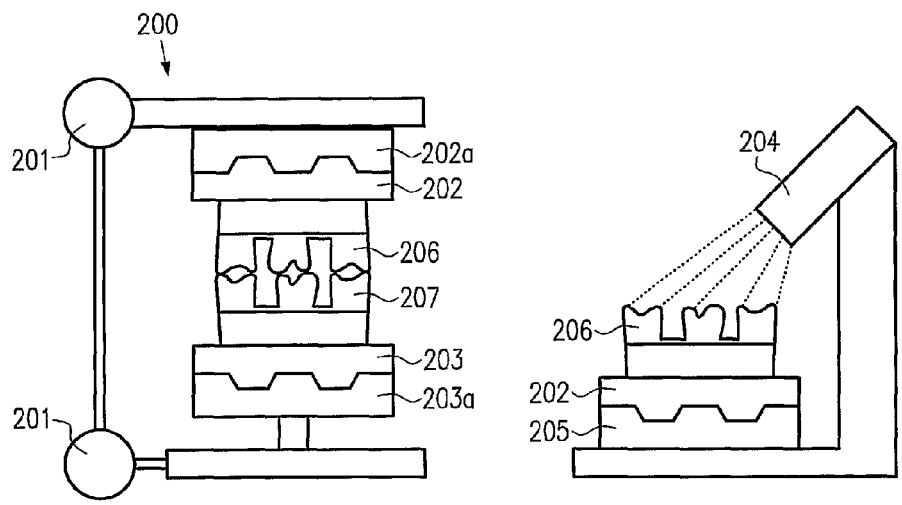
FIG. 11 is a diagrammatic lateral view of a masticatory and bite simulator in which another aspect of the invention is illustrated.
FIG. 12 shows a diagrammatic lateral view of a jaw of FIG. 11 in a surface mapping device.

Another aspect of the present invention relates to the automatic generation of the masticatory surface of a dental prosthesis, taking into consideration the counter bite (upper jaw to lower jaw). In the practical example illustrated in FIGS. 11 and 12, the following steps which will be described below are provided:

1. Insertion and adjustment of upper and lower jaws 206 and 207 in a masticatory simulator or articulator 200 with adjusting joints 201 until the bite situation is simulated, as shown in FIG. 11. Supports 202/202a and 203/203a for upper and lower jaws 206 and 207, respectively, have a detectable spatial position. Supports 202/202a and 202/203a, for example, have a defined zero position or a zero position with respect to each other. Each support 202/202a and 203/203a has two parts and comprises a supporting base 202a and 203a, each of which is stationary affixed to articulator 200, and a jaw support 202 and 203, to which upper jaw 206 and lower jaw 207, respectively, are attached.

2. Reading in/recording, e.g., 6 degrees of freedom:
   2 possibilities:—reading a scale manually
      reading out encoders Using articulator 200, the optimum/correct position of supports 202/202a and 202/203a, i.e., actually of the support base 202a and 203a, is determined while taking into account upper and lower jaws 206 and 207, respectively, as shown in FIG. 11. This can take place automatically with scales (not shown) which are provided on and are attached to articulator 200 or by means of position and phase-angle encoders (not shown). It should be noted that articulator 200 preferably allows an alignment of upper and lower jaws 206 and 207 with respect to each other in preferably six degrees of freedom.

3. Insertion of the respective jaw support 202 or 203 with the upper jaw model 206 or the lower jaw model 207 into a support 205 in correspondence with the support bases 202a and 203a of scanner 204 according to FIG. 12, whereby the spatial position of support 205 relative to the measuring system or the data system of scanner 204 is known.

4. Referencing is subsequently carried out by means of software.

5.—Proposal from the database for the masticatory surface (e.g., incisor)
   Automatic adjustment of the database model to the counter bite situation
   Search for contact points with envelope data
   Matching the masticatory surface to the internal data record
   Alternatively: record the position of the "articulated" jaw by means of scanning a portion of the articulated jaw and subsequently match the data of the upper and the lower jaws with these partial data records to produce the bite position.

The aspect of the invention explained with reference to FIGS. 11 and 12 is also to be considered as having been disclosed as part of the method and the device since a person skilled in the art can recognize suitable devices in general or special embodiments from the explanations given above.

The present invention is explained in the description and in the drawings on the basis of the practical examples solely by way of examples and is not limited thereto but comprises all variations, modifications, substitutions, and combinations that the person skilled in the art can gather from the present documents, in particular the claims and the general explanations in the introduction of this description and the description of the practical examples and the representations thereof in the drawing, and can combine, based on his or her expert knowledge as well as on prior art, in particular when including the complete disclosure contents of the previous applications cited in this description. In particular, all individual features and possibilities of the embodiments of the invention and the practical examples can be combined with one another.

What is claimed is:

1. A surface mapping and/or generating device characterized by devices for the process and/or cost optimisation, which comprise:
   means for incorporating measured data of the jaw bones using a suitable matching software; and
   means for simulating a planned treatment of the jaw using software, in which the teeth, the jaw, and the jaw bone are divided into groups of tooth and jaw sections, up to individual teeth, whereby the device is adapted to plan and simulate implants.

2. A surface mapping and/or generating device as set forth in claim 1, wherein the measured data of the jaw bones are data determined by a computed tomography.

3. A surface mapping and/or generating device as set forth in claim 1, wherein the groups and/or individual teeth can be moved and the final positions can be simulated.

4. A surface mapping and/or generating device as set forth in claim 3, wherein it can be simulated whether the space required is in fact present and/or how the patient will look after the treatment.

5. A surface mapping and/or generating device as set forth in claim 4, wherein an electronic data processing/software module is provided, that can be used for follow-up treatment, wherein images, taken over time can be displayed in the form of an interpolated film.

6. A surface mapping and/or generating method with the steps of:
   using devices for the process and/or cost optimisation by incorporating measured data of the jaw bones using a suitable matching software;
   simulating a planned treatment of a jaw using software, in which the teeth, the jaw, and the jaw bone are divided into groups of tooth and jaw sections, up to individual teeth, whereby implants can be planned and simulated.

7. A surface mapping and/or generating method as set forth in claim 6, wherein the measured data of the jaw bones are data determined by a computed tomography.

8. A surface mapping and/or generating method as set forth in claim 6, wherein the groups and/or individual teeth are moved and the final positions are simulated.

9. A surface mapping and/or generating method as set forth in claim 8, wherein it is simulated whether the space required is in fact present and/or how the patient will look after the treatment.

10. A surface mapping and/or generating method as set forth in claim 9, wherein an electronic data processing/software module is used for follow-up treatment.

11. A surface mapping and/or generating method as set forth in claim 10, wherein images are taken over time by scanning/mapping.

12. A surface mapping and/or generating method as set forth in claim 11, wherein the images obtained by scanning/mapping are displayed in the form of an interpolated film.

13. A surface mapping and/or generating method as set forth in claim 11, wherein the progress in the actual treatment can be compared to the planned treatment, and based on this comparison, potentially required corrections can be made.

14. A surface mapping method for generating images of teeth, comprising:
   scanning, using laser light, one or more teeth, generating a series of overlapping digital images taken from differing perspectives;
   integrating the series of overlapping digital images, using matching software, to form a three dimensional digital image of the one or more teeth and their relative locations;
   analyzing the overlap errors produced at different points of the one or more teeth to detect variations in spatial directions;
   calibrating to correct errors based on analyzed overlap; and
   simulating a planned therapeutic treatment of the one or more teeth.

15. The method of claim 14, wherein two different perspectives are scanned and integrated for each of the one or more teeth.

16. The method of claim 15, wherein each of said two different perspectives are a half-frame.

17. The method of claim 14, wherein a CCD device generates scan data.

18. The method of claim 14, wherein the one or more teeth are moved during scanning 19. The method of claim 14, wherein scanning is performed at an angle of 90 degrees relative to a direction of movement of the one or more teeth.

20. The method of claim 14, wherein said step of simulating includes generating a sequence of desired relative positioning of the one or more teeth.

* * * * *